(12) United States Patent
Agbodoe

(10) Patent No.: US 7,819,907 B2
(45) Date of Patent: Oct. 26, 2010

(54) DEVICE AND METHOD FOR FIXING ADJACENT BONE PLATES

(75) Inventor: Victor B. Agbodoe, Stoughton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 840 days.

(21) Appl. No.: 11/552,165

(22) Filed: Oct. 24, 2006

(65) Prior Publication Data

US 2007/0100344 A1 May 3, 2007

(51) Int. Cl.
*A61B 17/84* (2006.01)
(52) U.S. Cl. .......................................... 606/324; 606/71
(58) Field of Classification Search ............... 606/71, 606/282, 285, 75, 324; 411/337–339, 351, 411/372.5, 372.6, 522, 525, 526, 528, 529, 411/931, 933, 934, 945, 991, 992; 24/194, 24/329, 339–341, 437–441
See application file for complete search history.

(56) References Cited

U.S. PATENT DOCUMENTS

| 3,976,079 | A | | 8/1976 | Samuels |
| 4,842,465 | A | * | 6/1989 | Pease et al. .................. 411/337 |
| 5,360,020 | A | * | 11/1994 | Lee et al. ..................... 128/888 |
| 7,048,738 | B1 | * | 5/2006 | Wellisz et al. .................. 606/70 |
| 2002/0156475 | A1 | | 10/2002 | Lerch |
| 2002/0169455 | A1 | | 11/2002 | Bannerman |

* cited by examiner

*Primary Examiner*—Thomas C Barrett
*Assistant Examiner*—Andrew Yang

(57) ABSTRACT

A method and device for reattaching adjacent bone plates includes an inner seat, a pin, and an outer seat. The pin is fixedly connected to the inner seat. The outer seat is selectively connected to the pin so that adjacent bone plates are securely held in place between the inner seat and the outer seat. The outer seat includes a first outer seat and a second outer seat that are slidably connected together. The first outer seat has a slot. The second outer seat also has a slot. The first outer seat and the second outer seat are movable between a pin engaging position and a pin locking position.

21 Claims, 3 Drawing Sheets

DEVICE AND METHOD FOR FIXING ADJACENT BONE PLATES

CROSS-REFERENCE TO RELATED APPLICATIONS

Not applicable.

STATEMENT REGARDING FEDERALLY SPONSORED RESEARCH

Not Applicable.

FIELD OF THE INVENTION

The present invention relates to a device and method for fixing adjacent bone plates. More specifically, the present invention relates to a device and method for fixing adjacent bone plates with the use of a two-piece outer seat that moves between a pin engaging position and a pin locking position.

SUMMARY OF THE INVENTION

The present invention provides a method and device for reattaching adjacent bone plates including an inner seat, a pin, and an outer seat. The pin is fixedly connected to the inner seat. The outer seat is selectively connected to the pin so that adjacent bone plates are securely held in place between the inner seat and the outer seat. The outer seat includes a first outer seat and a second outer seat that are slidably connected together. The first outer seat has a slot. The second outer seat also has a slot. The first outer seat and the second outer seat are movable between a pin engaging position and a pin locking position.

BRIEF DESCRIPTION OF THE DRAWINGS

The invention can be more fully understood from the following detailed description taken in conjunction with the accompanying drawings, in which.

DETAILED DESCRIPTION OF THE INVENTION

Figure 1:
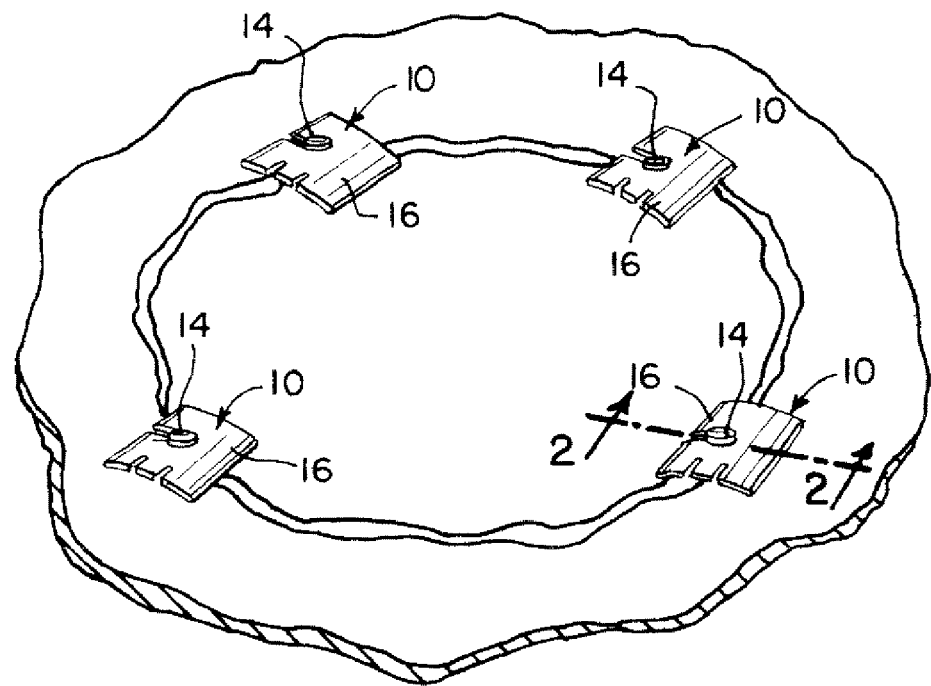
FIG. 1 is a perspective view showing the present invention being used to reattach adjacent bone plates.
Figure 2:
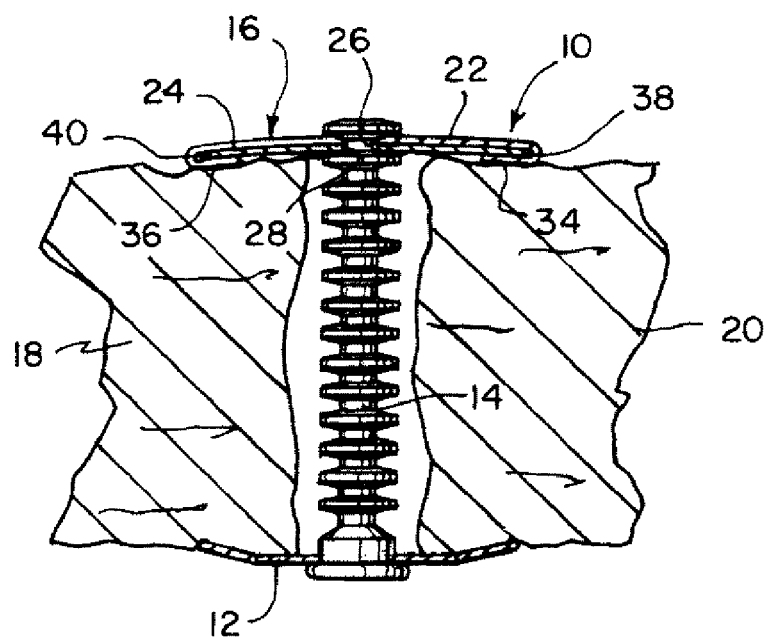
FIG. 2 is a cross-sectional view taken along lines 2-2 of FIG. 1 and looking in the direction of the arrows.
Figure 3:
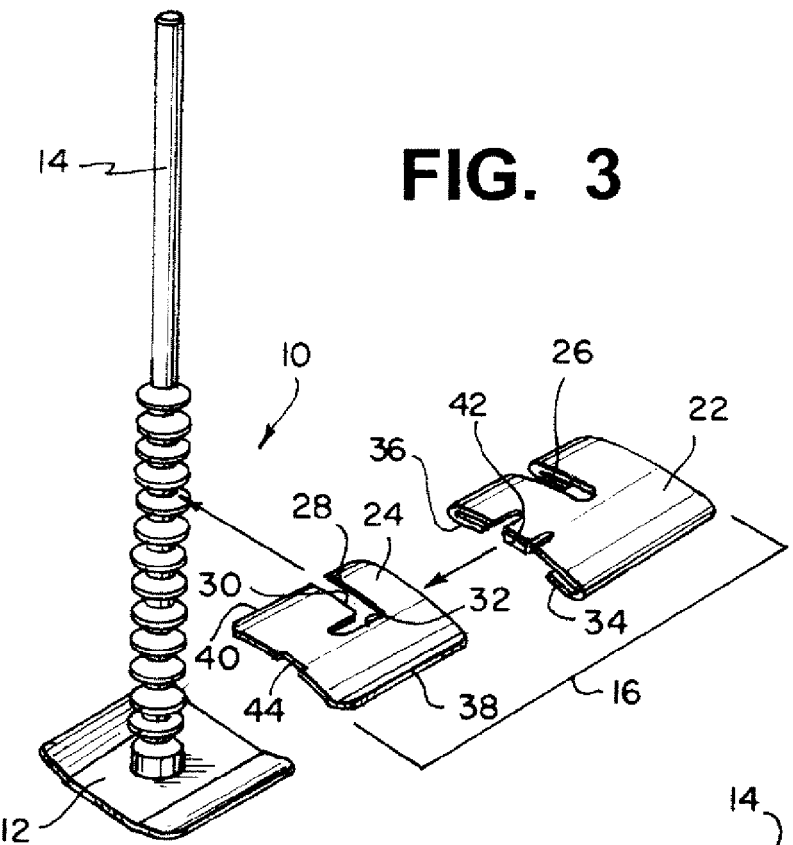
FIG. 3 is a perspective exploded view of the device and method of the present invention for fixing adjacent bone plates.

Referring now to FIGS. 1-5, a method and device 10 for reattaching adjacent bone plates in accordance with the present invention is illustrated. The device includes an inner seat 12, a pin 14, and an outer seat 16. Pin 14 is fixedly connected to inner seat 12. Outer seat 16 is selectively connected to pin 14 so that adjacent bone plates 18, 20 are securely held in place between the inner seat and the outer seat, as shown in FIG. 2. Inner seat 12 and outer seat 14 are preferably made of a biocompatible material, such as titanium. Inner seat 12 and outer seat 14 are preferably rectangular in shape. More preferably, inner seat 12 and outer seat 14 are square in shape.

Figure 4A:
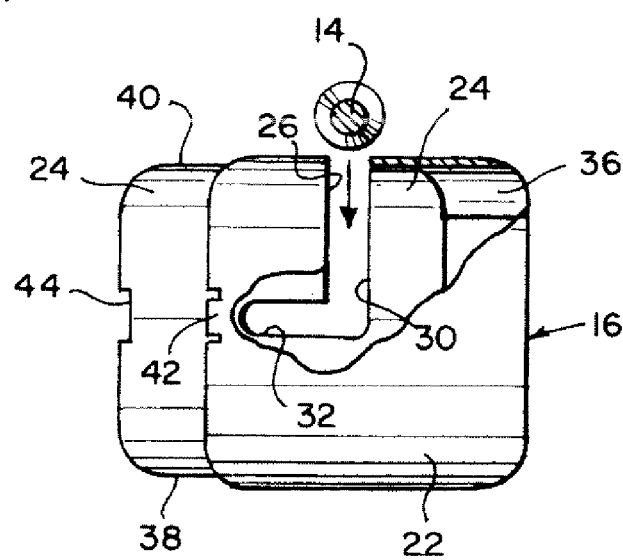
FIG. 4A is a top plan view, with sections broken away, showing the outer seat and pin before the outer seat is moved into position on the pin.
Figure 4B:
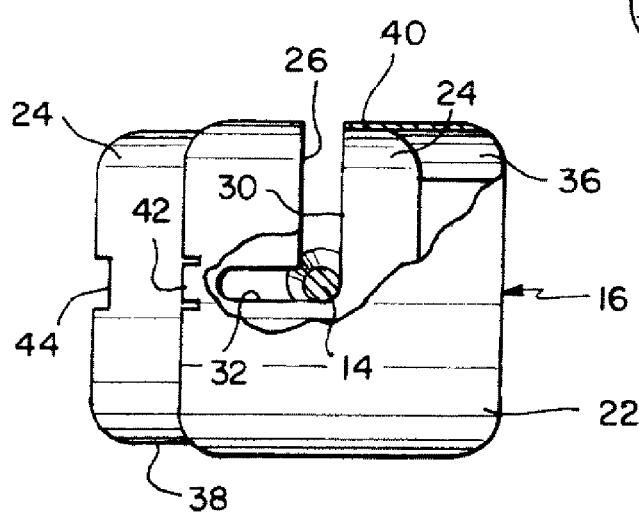
FIG. 4B is a top plan view, with sections broken away, of the outer seat and pin after the outer seat is moved into position on the pin and in the pin engaging position.

Outer seat 16 includes a first outer seat 22 and a second outer seat 24. First outer seat 22 has a slot 26. Second outer seat 24 has a slot 28. Slot 28 has a first portion 30 and a second portion 32. First portion 30 is approximately at a 90° angle with respect to second portion 32. First outer slot has a first flange 34 and a second flange 36. First outer seat 22 and second outer seat 22 are connected together, as illustrated in FIG. 4A and FIG. 4B. This position is referred to as the pin engaging position. In this pin engaging position, the outer edges 38, 40 of second outer seat are snugly received between the flanges 34, 36 with sufficient pressure that first outer seat 22 does not move with respect to second outer seat 24, without an externally applied force being applied. In the pin engaging position, slot 26 in the first outer seat 22 aligns with the first portion 30 of the slot 28 of the second outer seat 24, as shown in FIGS. 4A and 4B.

Figure 4C:
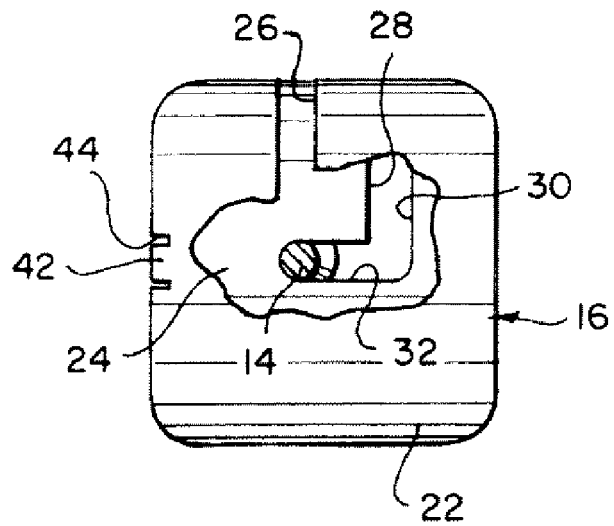
FIG. 4C is a top plan view, with sections broken away, of the outer seat and pin after the outer seat is moved into pin locking position.
Figure 5:
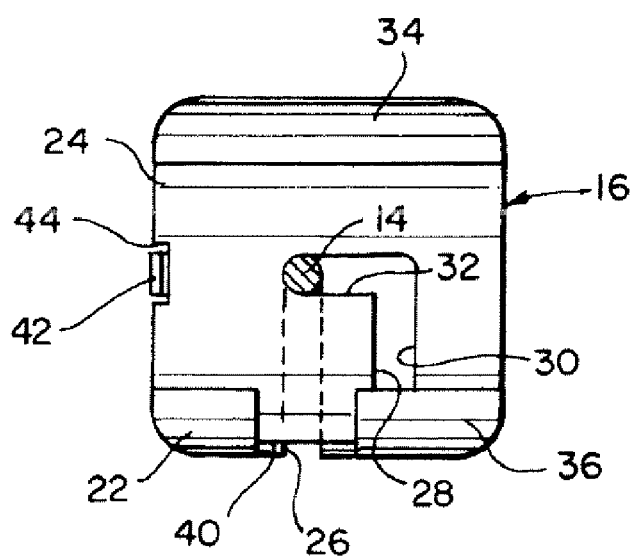
FIG. 5 is a bottom plan view, with sections broken away, of the outer seat and pin after the outer seat is moved into pin locking position.

First outer seat 22 is slidably connected to second outer seat 24. First outer seat 22 and the second outer seat 24 being movable between a pin engaging position (FIGS. 4A and 4B) and a pin locking position (FIGS. 4C and 5). First outer seat 22 includes a biased hook 42. Second outer seat 24 includes a mating notch 44. First outer seat 22 is slidably connected to the second outer seat 24, such that the first outer seat and the second outer seat are movable so that the outer seat 16 moves from the pin engaging position to the pin locking position. In the pin locking position, hook 42 interlocks with notch 42 to maintain the outer seat 16 in the pin locking position. In the pin locking position, slot 26 is no longer aligned with portion 30 of slot 28. In stead, slot 26 aligns only with a section of portion 32 of slot 28 as shown in FIGS. 4C and 5. In the pin locking position, first outer seat 22 and second outer seat 24 are rigidly held together due to the engaging of hook 42 in recess 44. Thereafter, the user can snip off the upperwardly projecting remaining portion of pin 14 in a manner known to those skilled in the art.

It will be understood that the foregoing is only illustrative of the principles of the invention, and that various modifications can be made by those skilled in the art without departing from the scope and spirit of the invention. All references cited herein are expressly incorporated by reference in their entirety.

One skilled in the art will appreciate further features and advantages of the invention based on the above-described embodiments. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps, which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. Accordingly, the invention is not to be limited by what has been particularly shown and described, except as indicated by the

What is claimed is:

1. A device for reattachment of adjacent bone plates comprising:
   an inner seat;
   a pin connected to said inner seat;
   an outer seat, said outer seat being selectively connected to said pin so that the adjacent bone plates are securely held in place between said inner seat and said outer seat, said outer seat including a first outer seat having an outer edge and a second outer seat having an outer edge that are connected together, said first outer seat having a slot that opens at said outer edge and is configured to receive said pin, said second outer seat having a slot that opens at said outer edge and is configured to receive said pin; and
   wherein the first outer seat is slidably connected to said second outer seat, said first outer seat and said second outer seat of said outer seat being movable between a pin engaging position and a pin locking position.

2. The device of claim 1, wherein said slot of said second outer seat comprises a first portion and a second portion disposed at an angle with respect to said first portion.

3. The device of claim 2, wherein in said pin engaging position, said slot in said first outer seat aligns with a first portion of said slot of said second outer seat.

4. The device of claim 3, wherein said first portion of said slot in said second outer seat is approximately at a 90° angle with respect to said second portion of said of said slot in said second outer seat.

5. The device of claim 1, wherein said first outer seat includes a biased hook.

6. The device of claim 5, wherein said second outer seat includes a notch.

7. The device of claim 1, wherein said first outer seat includes a biased hook, said second outer seat includes a notch, the first outer seat is slidably connected to said second outer seat, said first outer seat and said second outer seat of said outer seat being movable between a pin engaging position and a pin locking position, in said pin locking position said hook interlocking with said notch to maintain said outer seat in said pin locking position.

8. The device of claim 1, wherein said outer seat and said inner seat are rectangular in shape.

9. The device of claim 1, wherein said outer seat and said inner seat are square in shape.

10. A device for reattachment of adjacent bone plates comprising:
    an inner seat;
    a pin connected to said inner seat;
    an outer seat, said outer seat being selectively connected to said pin so that the adjacent bone plates are securely held in place between said inner seat and said outer seat, said outer seat including a first outer seat having an outer edge and a second outer seat having an outer edge that are connected together, said first outer seat having a slot that opens at said outer edge and is configured to receive said pin, said second outer seat having a slot that opens at said outer edge and is configured to receive said pin;
    wherein said slot of said second outer seat comprises a first portion and a second portion disposed at an angle with respect to said first portion;
    wherein in said pin engaging position, said slot in said first outer seat aligns with a first portion of said slot of said second outer seat; and
    wherein said first portion of said slot in said second outer seat is approximately at a 90° angle with respect to said second portion of said of said slot in said second outer seat.

11. The device of claim 10, wherein said first outer seat includes a biased hook.

12. The device of claim 11, wherein said second outer seat includes a notch.

13. The device of claim 10, wherein said first outer seat includes a biased hook, said second outer seat includes a notch, the first outer seat is slidably connected to said second outer seat, said first outer seat and said second outer seat of said outer seat being movable between a pin engaging position and a pin locking position, in said pin locking position said hook interlocking with said notch to maintain said outer seat in said pin locking position.

14. The device of claim 10, wherein said outer seat and said inner seat are rectangular in shape.

15. The device of claim 10, wherein said outer seat and said inner seat are square in shape.

16. A device for reattachment of adjacent bone plates comprising:
    an inner seat;
    a pin connected to said inner seat;
    an outer seat, said outer seat being selectively connected to said pin so that the adjacent bone plates are securely held in place between said inner seat and said outer seat, said outer seat including a first outer seat having an outer edge and a second outer seat having an outer edge that are connected together, said first outer seat having a slot that opens at said outer edge and is configured to receive said pin, said second outer seat having a slot that opens at said outer edge and is configured to receive said pin;
    wherein the first outer seat is slidably connected to said second outer seat, said first outer seat and said second outer seat of said outer seat being movable between a pin engaging position and a pin locking position; and
    wherein said first outer seat includes a biased hook, said second outer seat includes a notch, the first outer seat is slidably connected to said second outer seat, said first outer seat and said second outer seat of said outer seat being movable between a pin engaging position and a pin locking position, in said pin locking position said hook interlocking with said notch to maintain said outer seat in said pin locking position.

17. The device of claim 16, wherein said slot of said second outer seat comprises a first portion and a second portion disposed at an angle with respect to said first portion.

18. The device of claim 17, wherein in said pin engaging position, said slot in said first outer seat aligns with a first portion of said slot of said second outer seat.

19. The device of claim 18, wherein said first portion of said slot in said second outer seat is approximately at a 90° angle with respect to said second portion of said of said slot in said second outer seat.

20. The device of claim 16, wherein said outer seat and said inner seat are rectangular in shape.

21. The device of claim 16, wherein said outer seat and said inner seat are square in shape.

* * * * *